(12) United States Patent
Van Milligen et al.

(10) Patent No.: US 8,329,959 B2
(45) Date of Patent: Dec. 11, 2012

(54) PROCESS FOR THE PREPARATION OF ALKYLENE GLYCOL

(75) Inventors: Hendrik Johannes Van Milligen, Amsterdam (NL); Peter Veenstra, Amsterdam (NL)

(73) Assignee: Shell Oil Company, Houston, TX (US)

( * ) Notice: Subject to any disclaimer, the term of this patent is extended or adjusted under 35 U.S.C. 154(b) by 223 days.

(21) Appl. No.: 12/745,918

(22) PCT Filed: Dec. 5, 2008

(86) PCT No.: PCT/EP2008/066855
§ 371 (c)(1),
(2), (4) Date: Jul. 27, 2010

(87) PCT Pub. No.: WO2009/071651
PCT Pub. Date: Jun. 11, 2009

(65) Prior Publication Data
US 2010/0312022 A1 Dec. 9, 2010

(30) Foreign Application Priority Data

Dec. 6, 2007 (EP) .................................. 07122548

(51) Int. Cl.
C07C 29/09 (2006.01)
C07C 29/80 (2006.01)
(52) U.S. Cl. .................... 568/852; 568/858; 568/868
(58) Field of Classification Search ................ 568/858
See application file for complete search history.

(56) References Cited

U.S. PATENT DOCUMENTS

| 3,629,343 | A | 12/1971 | Zakharovich et al. | 260/635 |
|---|---|---|---|---|
| 4,160,116 | A | 7/1979 | Mieno et al. | 568/867 |
| 4,556,748 | A | 12/1985 | Tsang et al. | 568/858 |
| 6,080,897 | A | 6/2000 | Kawabe | 568/858 |
| 6,187,792 | B1 | 2/2001 | Delorme et al. | 514/320 |
| 6,187,972 | B1 | 2/2001 | Kawabe et al. | 568/858 |
| 2004/0267058 | A1 | 12/2004 | Harmsen et al. | 568/867 |

FOREIGN PATENT DOCUMENTS

| JP | 11269110 | 10/1999 |
|---|---|---|
| JP | 2001233831 | 8/2001 |
| WO | WO2004069777 | 8/2004 |

*Primary Examiner* — Shawquia Young

(57) ABSTRACT

The invention provides a process and a reactor for the preparation of an alkylene glycol from an alkylene oxide. Alkylene oxide, water, a homogeneous carboxylation catalyst and a homogenous hydrolysis catalyst are supplied to a reactor comprising a carboxylation zone and a hydrolysis zone. One or more ejectors are used to mix carbon dioxide and the liquid reagents in the carboxylation zone so that alkylene oxide reacts with carbon dioxide in the presence of water in the carboxylation zone to form a reaction solution comprising alkylene carbonate, water, the homogeneous carboxylation catalyst and the homogeneous hydrolysis catalyst. The reaction solution is supplied from the carboxylation zone to a hydrolysis zone, wherein alkylene carbonate and water react to form a product solution comprising alkylene glycol, the homogeneous carboxylation catalyst and the homogeneous hydrolysis catalyst. Carbon dioxide released by the reaction of alkylene carbonate and water in the hydrolysis zone is supplied to the carboxylation zone. Product solution is withdrawn from the hydrolysis zone.

9 Claims, 3 Drawing Sheets

PROCESS FOR THE PREPARATION OF ALKYLENE GLYCOL

PRIORITY CLAIM

The present application claims priority to European Patent Application 07122548.6 filed 6 Dec. 2007.

FIELD OF THE INVENTION

The present invention relates to a process for the preparation of an alkylene glycol from an alkylene oxide.

BACKGROUND OF THE INVENTION

Monoethylene glycol is used as a raw material in the manufacture of polyester fibres, polyethylene terephthalate (PET) plastics and resins. It is also incorporated into automobile antifreeze liquids.

Monoethylene glycol may be prepared in a highly selective process from ethylene oxide via ethylene carbonate. This is typically carried out in a two-step process wherein the first step is the reaction of ethylene oxide with carbon dioxide to form ethylene carbonate, and the second step is the hydrolysis of ethylene carbonate to form ethylene glycol.

In U.S. Pat. No. 6,080,897, ethylene oxide reacts with carbon dioxide to form ethylene carbonate in a carboxylation reaction apparatus consisting of a first bubble column, a second bubble column and a gas-liquid separator. The liquid phase from the separator is passed to a tubular reactor, and the reaction solution from the tubular reactor is passed to a hydrolysis apparatus composed of a first vessel and a second vessel connected in series. The carbon dioxide released in the hydrolysis reaction is compressed and recycled to the carboxylation reaction apparatus.

In JP 11-269110, ethylene oxide reacts with carbon dioxide and water in the presence of a catalyst to form ethylene carbonate and monoethylene glycol in a loop type reactor with an ejector. A part of the reaction solution is extracted from the lower portion of the reactor and the extracted portion is circulated using a pump and injected into the upper portion of the reactor via an ejector nozzle. Heat from the exothermic carboxylation reaction is removed by cooling the extracted reaction mixture in a heat exchanger. In the example, the reaction mixture from the reactor contained 61.1% monoethylene glycol and 37.1% ethylene carbonate. Subsequent hydrolysis and distillation provided high quality monoethylene glycol. A similar system is disclosed in JP 2001 233831.

The present inventors have sought to further improve the manufacture of alkylene glycol from alkylene oxide.

SUMMARY OF THE INVENTION

Accordingly, the present invention provides a process for the preparation of an alkylene glycol from an alkylene oxide, comprising steps of
(a) supplying alkylene oxide, water, a homogeneous carboxylation catalyst and a homogenous hydrolysis catalyst as liquid reagents to a carboxylation zone of a reactor,
(b) using one or more ejectors to mix carbon dioxide and the liquid reagents in the carboxylation, zone so that alkylene oxide reacts with carbon dioxide in the presence of water to form a reaction solution comprising alkylene carbonate, water, the homogeneous carboxylation catalyst and the homogeneous hydrolysis catalyst;
(c) supplying the reaction solution from the carboxylation zone to a hydrolysis zone of a reactor, wherein alkylene carbonate and water react to form a product solution comprising alkylene glycol, the homogeneous carboxylation catalyst and the homogeneous hydrolysis catalyst;
(d) supplying carbon dioxide released by the reaction of alkylene carbonate and water in the hydrolysis zone to the carboxylation zone; and
(e) withdrawing the product solution from the hydrolysis zone.

The present invention further provides a reactor for the preparation of an alkylene glycol from an alkylene oxide, comprising
(a) a carboxylation zone comprising one or more inlets for liquid reagents comprising alkylene oxide, water, a homogeneous carboxylation catalyst and a homogenous hydrolysis catalyst, one or more inlets for carbon dioxide, one or more ejectors for mixing carbon dioxide with the liquid reagents, and one or more outlets for a reaction solution comprising alkylene carbonate, water, the homogeneous carboxylation catalyst and the homogeneous hydrolysis catalyst;
(b) a hydrolysis zone comprising one or more inlets for the reaction solution, one or more outlets for carbon dioxide, and one or more outlets for a product solution comprising alkylene glycol, the homogeneous carboxylation catalyst and the homogeneous hydrolysis catalyst; and
(c) a channel whereby carbon dioxide can be supplied from the hydrolysis zone to the carboxylation zone.

The process and reactor of the invention can achieve high conversion of alkylene oxide to alkylene glycol in a relatively simple and small apparatus, thereby reducing capital expenditure.

DETAILED DESCRIPTION OF THE INVENTION

Figure 1:
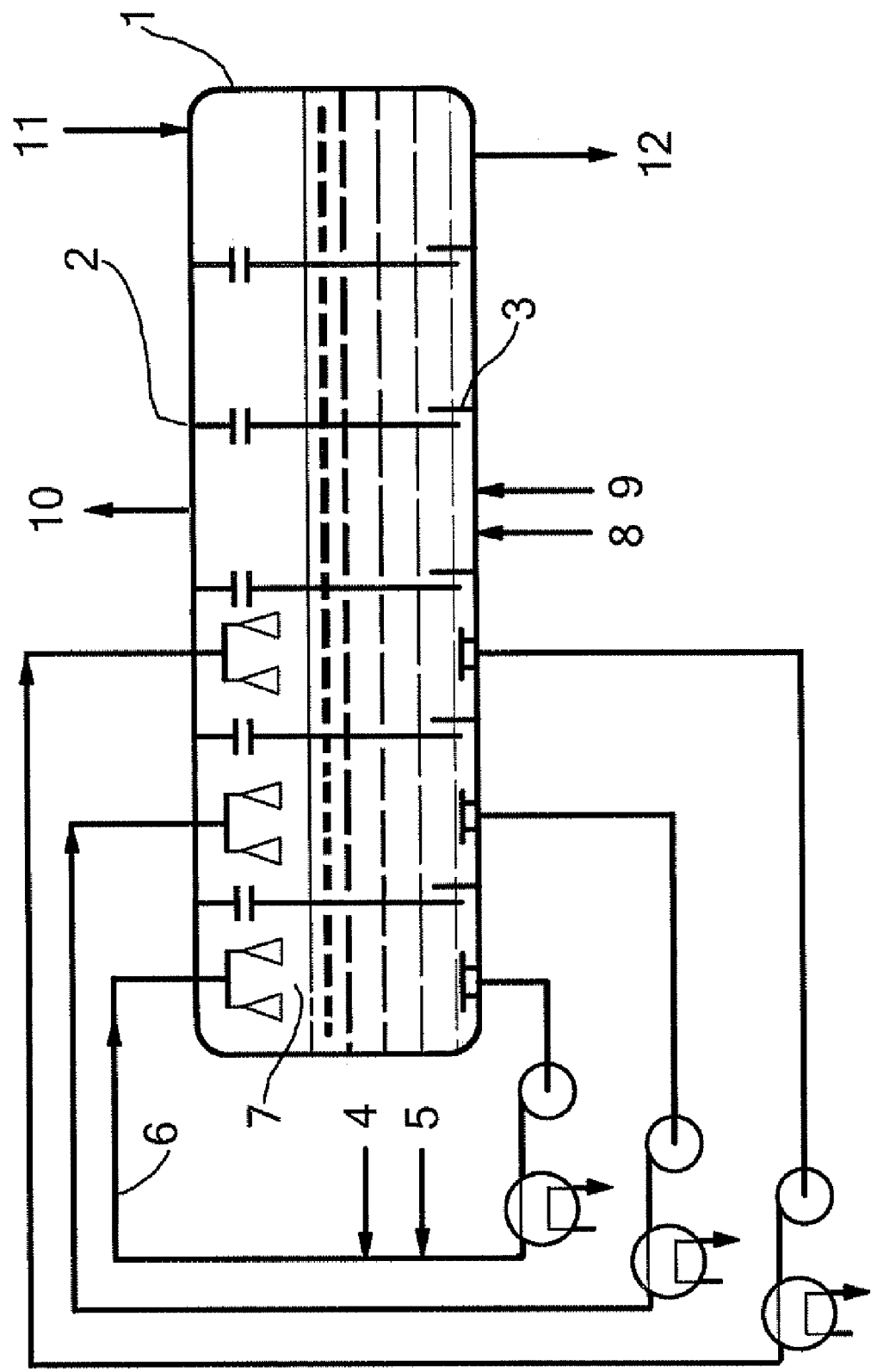
FIG. 1 is a schematic diagram showing a reactor and process according to a first embodiment of the invention.

The process and reactor of the invention uses one or more ejectors to mix carbon dioxide and the liquid reagents in the carboxylation zone. The carbon dioxide is supplied to the carboxylation zone from the hydrolysis zone, where it is released during the reaction of alkylene carbonate and water. An ejector is a device wherein a motive fluid passes through a converging-diverging nozzle, creating a low pressure that draws in and entrains a suction fluid. Use of one or more ejectors ensures mixing of carbon dioxide (present in the vapour phase) with the ethylene oxide and promotes the carboxylation reaction. Additionally, some ethylene oxide is present in the vapour phase and the ejectors mix the gaseous ethylene oxide with the liquid reagents.

The present invention provides a process for the preparation of an alkylene glycol from an alkylene oxide, proceeding via an alkylene carbonate intermediate:

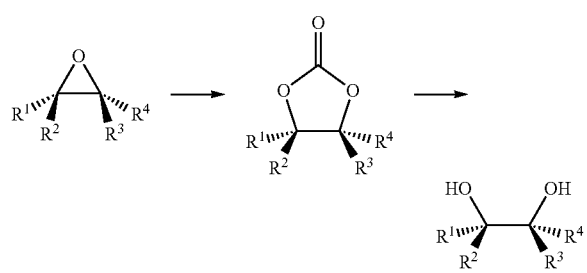

$R^1$, $R^2$, $R^3$ and $R^4$ may independently be chosen from hydrogen or an optionally substituted alkyl group having from 1 to 6 carbon atoms, preferably from 1 to 3 carbon atoms. As substituents, moieties such as hydroxy groups may be present. Preferably, $R^1$, $R^2$ and $R^3$ represent hydrogen atoms and $R^4$ represents hydrogen or a non-substituted $C_1$-$C_3$-alkyl group and, more preferably, $R^1$, $R^2$, $R^3$ and $R^4$ all represent hydrogen atoms.

Examples of suitable alkylene oxides therefore include ethylene oxide and propylene oxide. In the present invention the most preferred alkylene oxide is ethylene oxide.

The terms "carboxylation zone" and "hydrolysis zone" are used to describe regions in one or more reactor vessels wherein, respectively, carboxylation of alkylene oxide and hydrolysis of alkylene carbonate occur. In practice, the regions where carboxylation and hydrolysis occur may overlap (i.e. carboxylation and hydrolysis may occur in the same region). However, the terms "carboxylation zone" and "hydrolysis zone" indicate regions wherein predominantly carboxylation occurs and wherein predominantly hydrolysis occurs. The hydrolysis zone is downstream of the carboxylation zone. Each zone consists of a liquid phase, wherein the carboxylation or hydrolysis reaction occurs, and a gas phase above the liquid phase. In the carboxylation zone preferably at least 80 wt % of alkylene oxide supplied to the carboxylation zone reacts with carbon dioxide to form alkylene carbonate. In the hydrolysis zone preferably at least 80 wt % of alkylene carbonate in the reaction solution from the carboxylation zone reacts with water to form alkylene glycol.

The carboxylation zone and hydrolysis zone in the process and reactor of the invention may be contained in more than one reactor vessel (e.g. the carboxylation zone may be in a first reaction vessel and the hydrolysis zone may be in a second reaction vessel), but in a preferred embodiment of the invention, the carboxylation zone and the hydrolysis zone are contained within one reactor vessel. The reactor of the invention may comprise only two compartments (one compartment that forms the carboxylation zone and one compartment that forms the hydrolysis zone), but the reactor is preferably divided into at least four compartments, and most preferably the reactor of the invention is a single reactor vessel divided into at least four compartments. The term "compartment" is used to describe a subdivision of the volume of a reactor through which the liquids must pass, e.g. if the reactor has four compartments, reaction liquids must travel through each of the four compartments in turn before exiting the reactor. Dividing the reactor into compartments increases conversion for a given reactor volume or can maintain the conversion level with a smaller reactor volume, so improves the economics of the process. The carboxylation zone preferably comprises at least the first compartment of a reactor having at least four compartments. (The term "first compartment" is used to describe the compartment that is furthest upstream.) The hydrolysis zone preferably comprises at least the final compartment of a reactor having at least four compartments. (The term "final compartment" is used to describe the compartment that is furthest downstream.) Preferably the reactor has at least 6 compartments and more preferably the reactor has at least 8 compartments. Preferably the reactor has less than 30 compartments.

The reactor of the invention is preferably divided into compartments by internal baffles. Preferably the carboxylation zone is separated from the hydrolysis zone by an internal baffle. In one embodiment of the invention the internal baffles provide a sinuous or tortuous route for reaction liquids through the reactor. In a preferred embodiment, the compartments in the reactor are formed by a series of alternating first internal baffles and second internal baffles that provide a sinuous route for reaction liquid through the reactor. In a most preferred embodiment the reaction liquids pass under the first internal baffles and reaction fluids pass over the second internal baffles. For example, the first internal baffles may be downwardly extending baffles and the second internal baffles may be upwardly extending baffles.

Alkylene oxide, water, a homogeneous carboxylation catalyst and a homogeneous hydrolysis catalyst are supplied as liquid reagents to the carboxylation zone of a reactor. Preferably the reactor of the invention comprises at least one recycle loop whereby liquid reagents are withdrawn from the carboxylation zone and subsequently returned to the carboxylation zone. If the reactor is divided into compartments, preferably each compartment in the carboxylation zone has at least one recycle loop whereby liquid reagents are withdrawn from the carboxylation zone and subsequently returned to the carboxylation zone. The one or more recycle loops will continually resupply the liquid reagents to the carboxylation zone. However, as the reagents will be consumed in the carboxylation reaction and/or will leave the carboxylation zone as part of the reaction product, it is necessary to supply alkylene oxide, water, homogeneous carboxylation catalyst and homogeneous hydrolysis catalyst from external sources to the carboxylation zone. The liquid reagents from external sources are preferably supplied to at least one of one or more recycle loops. If the reactor is divided into compartments, preferably the liquid reagents from external sources are supplied to the compartment that is furthest upstream in the carboxylation zone, most preferably via a recycle loop that resupplies liquid reagents to that compartment.

An advantage of recycle loops is that they enable control of the temperature in the carboxylation zone because the liquids in the one or more of the recycle loops can be subjected to heat exchange. The carboxylation reaction is exothermic, so preferably heat is withdrawn (and preferably recovered) from one or more recycle loops that are connected to the most upstream compartment(s) in the carboxylation zone. It may be preferred to supply heat to compartments that are further downstream in the carboxylation zone as less reaction may occur and the exotherm may thus be smaller.

Another advantage of recycle loops is that they promote mixing of the liquid reagents.

The molar ratio of alkylene oxide to water supplied to the carboxylation zone (from external sources, i.e. not via a recycle loop) is preferably between 1:5 and 2:1, more preferably between 1:2 and 1.2:1, most preferably about 1:1.

Homogeneous catalysts that are known to promote carboxylation include alkali metal halides such as potassium iodide and potassium bromide, and halogenated organic phosphonium or ammonium salts such as tributylmethylphosphonium iodide, tetrabutylphosphonium iodide, triphenylmethylphosphonium iodide, triphenylpropylphosphonium bromide, triphenylbenzylphosphonium chloride, tetraethylammonium bromide, tetramethylammonium bromide, benzyltriethylammonium bromide, tetrabutylammonium bromide and tributylmethylammonium iodide. Homogeneous catalysts that are known to promote hydrolysis include basic alkali metal salts such as potassium carbonate, potassium hydroxide and potassium bicarbonate, or alkali metal metalates such as potassium molybdate. It is possible that one catalyst could be employed as both the homogeneous carboxylation catalyst and the homogeneous hydrolysis catalyst, but it is preferred that different catalysts are employed as the homogeneous carboxylation catalyst and the homogeneous hydrolysis catalyst. Preferred homogeneous catalyst systems include a combination of potassium iodide and potassium carbonate, and a combination of potassium iodide and potassium molybdate. The catalysts are preferably supplied as a catalyst mixture dissolved in alkylene glycol.

The molar ratio of carboxylation catalyst to alkylene oxide that is supplied to the carboxylation zone from external sources (i.e. not via a recycle loop) is preferably between 1:1000 and 1:20. The molar ratio of hydrolysis catalyst to alkylene oxide that is supplied to the carboxylation zone from external sources (i.e. not via a recycle loop) is preferably between 1:1000 and 1:20.

Carbon dioxide is supplied to the carboxylation zone from the hydrolysis zone. Carbon dioxide is mixed with the liquid reagents in the carboxylation zone so that alkylene oxide reacts with carbon dioxide in the presence of water to form a reaction solution comprising alkylene carbonate, water, the homogeneous carboxylation catalyst and the homogeneous hydrolysis catalyst. Mixing of carbon dioxide in the liquid phase is achieved using one or more ejectors. An ejector is a device wherein a motive fluid passes through a converging-diverging nozzle, creating a low pressure that draws in and entrains a suction fluid. In the present invention, the motive fluid is the liquid reagents, and the suction fluid is a gas comprising carbon dioxide. Ejectors can be mounted inside the reactor, such that there is suction of gases present in the vapour space inside the reactor. Ejectors can alternatively be mounted such that the suction takes place outside the reactor. An advantage of mounting the ejector inlets outside the reactor is that they are easier to maintain. The outlets of the ejectors are inside the reactor and can be positioned such that the fluids leaving the ejectors enter the gas phase in the reactor or enter the liquid phase in the reactor. Preferably the mixing is achieved using more than one ejector, and most preferably ejectors are used in all compartments in the carboxylation zone. Each compartment may use the same type of ejector, but different types of ejectors (i.e. ejectors wherein suction occurs inside/outside the reactor, ejectors having outlets into the gas phase/liquid phase) can be used in different compartments.

The reaction solution from the carboxylation zone is supplied to a hydrolysis zone of a reactor. Preferably the reaction solution is supplied from the carboxylation zone to the hydrolysis zone without changing the pressure of the reaction solution, i.e. there is no requirement to pump the reaction solution from the carboxylation zone to the hydrolysis zone. In a preferred embodiment of the invention, the carboxylation zone and the hydrolysis zone are both contained in a single reactor vessel, and the reaction solution passes from the carboxylation zone to the hydrolysis zone by passing through compartments in the reactor vessel. A single reactor vessel is preferred because a simpler system is likely to have lower capital costs. However, the process of the invention may also be carried out in a system wherein the carboxylation zone is in a first reactor vessel and the hydrolysis zone is in a second reactor vessel, and the reaction solution is supplied from the carboxylation zone to the hydrolysis zone by withdrawing the reaction solution from the first reactor vessel and supplying the reaction solution to the second reactor vessel.

Preferably, additional water is supplied to the hydrolysis zone, most preferably in the form of steam or hot water. Additional water promotes the hydrolysis reaction, and it is preferred that hot water is supplied because the hydrolysis reaction is endothermic. Preferably the molar ratio of the overall amount of water supplied from external sources (i.e. not via recycle loops) to both the carboxylation zone and the hydrolysis zone to the amount of alkylene oxide supplied from external sources to the carboxylation zone is between 5:1 and 1:1, preferably about 1.8:1. Greater amounts of water are not preferred because of the increased water removal requirement (and associated costs).

Carboxylation catalyst and hydrolysis catalyst are supplied to the hydrolysis zone as components of the reaction solution. However, in one embodiment of the invention, additional catalyst is supplied to the hydrolysis zone. The additional catalyst is preferably carboxylation catalyst and hydrolysis catalyst, and is most preferably the same mixture of carboxylation catalyst and hydrolysis catalyst as is supplied to the carboxylation zone. Addition of the catalyst mixture directly to the hydrolysis zone has the advantage of increasing the concentration of hydrolysis catalyst in the hydrolysis zone and further encouraging the hydrolysis reaction.

Preferably, gases are withdrawn from either the carboxylation zone or the hydrolysis zone to provide an inerts vent. By withdrawing a small proportion of the gases it is possible to prevent build-up of gases such as oxygen, methane and ethylene. The inerts are preferably withdrawn from the reactor at a point where the amount of alkylene oxide in the gas phase is low and where the inert gases are concentrated. If the carboxylation zone consists of several compartments, then it is preferred to position the inerts vent in the final compartment of the carboxylation zone (i.e. the compartment that is furthest downstream). Alternatively, the inerts vent can be positioned in the hydrolysis zone. Because some carbon dioxide will be removed from the system via an inerts vent, it is also preferred that make-up carbon dioxide is supplied to either the carboxylation zone or to the hydrolysis zone to make up the quantity of carbon dioxide that is removed.

Carbon dioxide released by the reaction of alkylene carbonate and water in the hydrolysis zone is supplied to the carboxylation zone. Preferably the carbon dioxide does not pass through a gas compressor. The term "gas compressor" is used to describe a mechanical device that increases the pressure of a gas by reducing its volume, and includes centrifugal compressors, axial compressors, reciprocating compressors, rotary screw compressors and scroll compressors. An ejector is not a gas compressor. Preferably, the carboxylation zone and the hydrolysis zone are in the same reactor vessel, and the gas phase of the carboxylation zone is separated from the gas phase of the hydrolysis zone by a baffle. In one embodiment, there is an opening in the baffle, preferably a short pipe through the baffle, and carbon dioxide is supplied from the hydrolysis zone to the carboxylation zone via the opening in the baffle. In an alternative embodiment, there are no openings in the baffle and carbon dioxide is supplied from the hydrolysis zone to the carboxylation zone via piping connecting the hydrolysis zone and the carboxylation zone. In this embodiment the carbon dioxide may be subjected to heat exchange (preferably cooling) before it is supplied to the carboxylation zone.

There is preferably a temperature profile across the reactor such that the temperature increases from the inlet to the outlet and the temperature in the hydrolysis zone is greater than the temperature in the carboxylation zone. Preferably the temperature at the reactor inlet will be from 80 to 120° C., most preferably about 100° C. Preferably the temperature at the reactor outlet will be from 130 to 170° C., most preferably about 150° C. The pressure in the reactor is typically from 0.1 to 3 MPa, preferably from 0.1 to 2 MPa and most preferably from 0.5 to 2 MPa.

The product solution is withdrawn from the reactor. Preferably the process of the invention achieves greater than 99% conversion of alkylene oxide to alkylene glycol, most preferably greater than 99.9%.

The product stream is preferably supplied to a dehydrator to remove water. The dehydrator is preferably one or more columns, including at least one vacuum column, preferably operating at a pressure of less than 0.05 MPa, more preferably less than 0.025 MPa and most preferably about 0.0125 MPa.

Preferably the carboxylation and hydrolysis catalysts are separated from the product stream by subjecting the product stream to a flash step in a flash vessel. A solution of the carboxylation and hydrolysis catalysts in alkylene glycol is preferably recycled and supplied to the carboxylation zone. The flash vessel is preferably at pressure of from 0.001 to 0.2 MPa, preferably from 0.005 to 0.1 MPa.

After dehydration and catalyst removal, the product stream is preferably purified to remove impurities and provide a purified alkylene glycol product stream.

FIG. 1 shows a reactor vessel (1) containing a liquid phase (shaded) and a gaseous phase above the liquid phase. The reactor vessel is divided into compartments by downwardly extending baffles (2) and upwardly extending baffles (3). Ethylene oxide and water are supplied at (4) and a mixture of homogeneous carboxylation and hydrolysis catalysts is supplied at (5) to a recycle loop (6) recycling liquids from and to the first compartment of the reactor. The mixture of catalysts is recycled from a downstream separation of catalyst from the product mixture (not shown). The recycle loop (6) consists of an outlet for withdrawing liquids from the compartment, a pump for pumping liquid around the loop and a heat exchanger for controlling the temperature of the liquid recycled to the compartment. Liquids are reintroduced to the first compartment via ejectors (7), which draw in gases from the vapour phase in the first compartment. Use of the ejectors ensures mixing of carbon dioxide (present in the vapour phase) with the ethylene oxide. Similar recycle loops and ejectors are present for the second and third compartments of the reactor vessel (1).

Additional catalyst (8) and steam (9) are supplied to the fourth compartment of the reactor vessel (1). The catalyst supplied at (8) is the same mixture of homogeneous carboxylation and hydrolysis catalysts as supplied to the carboxylation zone at (5) and is also recycled from the downstream separation of catalyst from the product mixture (not shown). Inerts are vented (10) from the fourth compartment of the reactor vessel (1). Carbon dioxide is supplied (11) to the final compartment of the reactor vessel (1). There are short pipes through the downwardly extending baffles (2), so gases can pass between the different compartments in the reactor vessel (1).

Ethylene oxide reacts with carbon dioxide in the presence of the carboxylation catalyst in the first, second and third compartments of the reactor vessel (1) and these essentially form the carboxylation zone in the reactor. The reaction is promoted by the mixing of carbon dioxide and ethylene oxide achieved by the recycle of the liquids (6) and by the ejectors (7). The temperature of the carboxylation zone is controlled by the heat exchangers in the recycle loops (6). Because the carboxylation reaction is exothermic, heat is removed by the two heat exchangers in the recycle loops for the first and second compartments. However, less carboxylation will occur in the third compartment, so the heat exchanger for the recycle loop for the third compartment will add heat to the recycled liquids.

The addition of additional catalyst (8) and steam (9) to the fourth compartment promotes hydrolysis of ethylene carbonate to ethylene glycol in the fourth, fifth and sixth compartments of the reactor vessel (1) and these essentially form the hydrolysis zone in the reactor. Carbon dioxide is released by the hydrolysis reaction, and the carbon dioxide passes to the carboxylation zone via the short pipes in the downwardly extending baffles (2). Inerts are vented (10) from the fourth compartment and carbon dioxide is supplied (11) to the sixth compartment to make up for carbon dioxide lost via the inerts vent.

The product stream comprising ethylene glycol, hydrolysis catalyst and carboxylation catalyst is withdrawn (12) from the sixth compartment of the reactor vessel (1).

Figure 2:
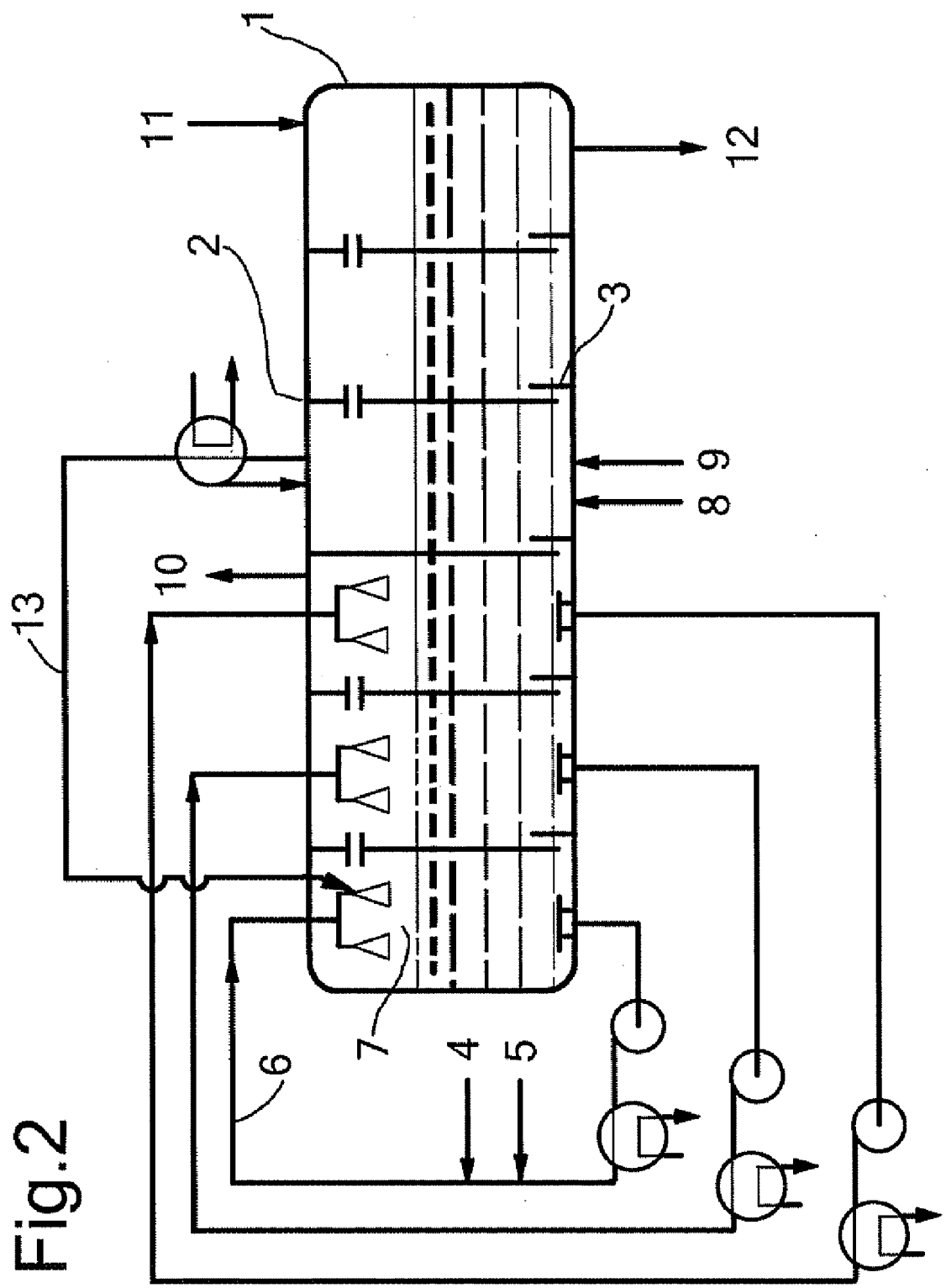
FIG. 2 is a schematic diagram showing a reactor and process according to a second embodiment of the invention.

The reactor and process shown in FIG. 2 have most of the same components and features as the reactor and process shown in FIG. 1. However, in FIG. 2 the downwardly extending baffle between the third and fourth compartments in the reactor vessel (1), i.e. the downwardly extending baffle between the carboxylation zone and the hydrolysis zone, does not have any openings above the liquid phase through which carbon dioxide can pass. Therefore, carbon dioxide produced in the hydrolysis zone cannot pass directly from the vapour phase of the hydrolysis zone to the vapour phase of the carboxylation zone. Instead, gases from the fourth compartment can pass to the first compartment via piping (13) connecting the first and fourth compartments. A heat exchanger cools the gases as they pass through the piping (13) and any condensed water can be removed (and resupplied to the fourth compartment) rather than being passed to the first compartment. The inerts vent (10) is located in the third compartment of the reactor vessel (1).

Figure 3:
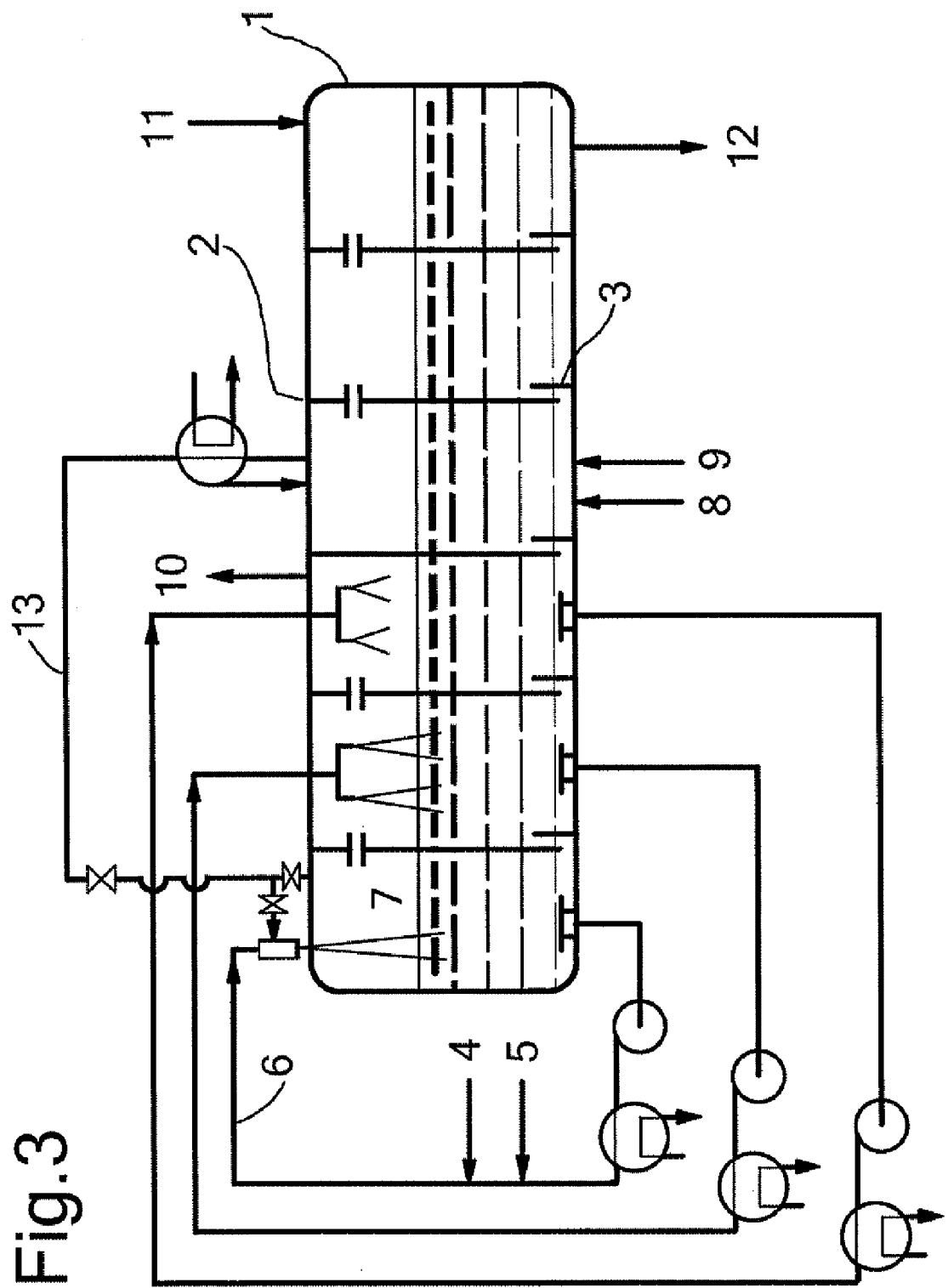
FIG. 3 is a schematic diagram showing a reactor and process according to a third embodiment of the invention.

The reactor and process shown in FIG. 3 have most of the same components and features as the reactor and process shown in FIG. 2. However, three different types of ejectors (7) are shown in the first, second and third compartments. The ejector in the first compartment of the reactor (1) is mounted such that the inlets are outside the reactor (1) and the outlet is inside the reactor (1). The motive fluid, comprising the liquid reagents, is supplied by the recycle loop (6). The suction fluid, gases including carbon dioxide, is provided from piping (13). The gases can be provided to piping (13) from both the first compartment and the fourth compartment of the reactor, and the supply is controlled by valves. The outlet of the ejector in the first compartment is directly into the liquid phase. The ejectors in the second compartment of the reactor (1) are mounted such that they are wholly within the reactor. The ejectors suck in gases from the vapour phase and the fluids are ejected into the liquid phase. The ejectors in the third compartment of the reactor (1) are mounted such that they are wholly within the reactor. The ejectors suck in gases from the vapour phase and the fluids are ejected into the vapour phase. Each type of ejector achieves the aim of mixing carbon dioxide with the liquid reagents. This figure shows specific ejector types in specific compartments, but alternative embodiments can be envisaged wherein the different ejector types are used in different compartments.

The invention will now be described by reference to examples which are not intended to be limiting of the invention. The examples were obtained by computer simulation (using Aspen modelling software) of the reactor shown in FIG. 2. The reactor was simulated as six continuously stirred tank reactors (CSTRs) in series. Vapour phase from the third CSTR was vented. Vapour phase from the last three CSTRs was combined with make-up carbon dioxide and fed to the first CSTR, without intermediate water condensation. All CSTRs were operated at 2.0 MPa (gauge). The reaction temperature was increased stepwise from 100° C. in the first CSTR to 150° C. in the last CSTR. The overall liquid residence time was selected such that the ethylene carbonate concentration in the liquid effluent of the last CSTR was less than 1 ppm mole. The carboxylation catalyst was potassium iodide and the hydrolysis catalyst was potassium molybdate.

EXAMPLE 1

Ethylene oxide, make-up carbon dioxide, water, carboxylation catalyst and hydrolysis catalyst were fed to the first CSTR in a molar ratio of 1.0:0.5:1.8:0.014:0.0029. No further water addition or catalyst addition was applied to any of the other CSTRs. Selectivity to monoethylene glycol was 99.2%. Ethylene oxide losses via the vent amounted to 1.6% of the ethylene oxide feed.

EXAMPLE 2

Ethylene oxide, make-up carbon dioxide, water, carboxylation catalyst and hydrolysis catalyst were fed to the first CSTR in a molar ratio of 1.0:0.5:1.5:0.014:0.0014. The same amounts of carboxylation catalyst and hydrolysis catalyst and 20% of the amount of water fed to the first CSTR were also fed to the third CSTR. Selectivity to monoethylene glycol was 99.5%. Ethylene oxide losses via the vent amounted to 1.0% of the ethylene oxide feed.

EXAMPLE 3

Ethylene oxide, make-up carbon dioxide, water, carboxylation catalyst and hydrolysis catalyst were fed to the first CSTR in a molar ratio of 1.0:0.5:1.0:0.014:0.0014. The same amounts of carboxylation catalyst and hydrolysis catalyst fed to the first CSTR were also fed to the third CSTR. Furthermore 80% of the amount of water fed to the first CSTR was also fed to the third CSTR. Selectivity to monoethylene glycol was 99.8%. Ethylene oxide losses via the vent amounted to 0.2% of the ethylene oxide feed.

What is claimed is:

1. A process for the preparation of an alkylene glycol from an alkylene oxide, comprising steps of
    (a) supplying alkylene oxide, water, a homogeneous carboxylation catalyst and a homogeneous hydrolysis catalyst as liquid reagents to a carboxylation zone of a reactor,
    (b) using one or more ejectors to mix carbon dioxide and the liquid reagents in the carboxylation zone so that alkylene oxide reacts with carbon dioxide in the presence of water to form a reaction solution comprising alkylene carbonate, water, the homogeneous carboxylation catalyst and the homogeneous hydrolysis catalyst;
    (c) supplying the reaction solution from the carboxylation zone to a hydrolysis zone of a reactor, wherein alkylene carbonate and water react to form a product solution comprising alkylene glycol, the homogeneous carboxylation catalyst and the homogeneous hydrolysis catalyst;
    (d) supplying carbon dioxide released by the reaction of alkylene carbonate and water in the hydrolysis zone to the carboxylation zone; and
    (e) withdrawing the product solution from the hydrolysis zone.

2. A process according to claim 1, wherein the carboxylation zone and the hydrolysis zone are contained within one reactor vessel.

3. A process according to claim 2, wherein the single reactor vessel is divided into at least four compartments by internal baffles.

4. A process according to claim 1, wherein the reactor comprises at least one recycle loop whereby liquid reagents are withdrawn from the carboxylation zone and subsequently returned to the carboxylation zone.

5. A process according to claim 1, wherein carbon dioxide is supplied from the hydrolysis zone to the carboxylation zone without passing through a gas compressor.

6. A process according to claim 1, wherein the hydrolysis zone comprises one or more inlets whereby steam is supplied to the hydrolysis zone, and the hydrolysis zone comprises one or more inlets whereby carboxylation catalyst and hydrolysis catalyst (in addition to the catalysts supplied in the reaction solution) are supplied to the hydrolysis zone.

7. A process according to claim 1, wherein either the carboxylation zone or the hydrolysis zone has an inerts vent whereby gases are withdrawn.

8. A process according to claim 1, wherein carbon dioxide is supplied from the hydrolysis zone to the carboxylation zone via an opening in a baffle separating the gas phase of the carboxylation zone from the gas phase of the hydrolysis zone, or wherein carbon dioxide is supplied from the hydrolysis zone to the carboxylation zone via external piping connecting the hydrolysis zone and the carboxylation zone.

9. A process according to claim 1, wherein the carboxylation and hydrolysis catalysts are separated from the product stream by subjecting the product stream to a flash step in a flash vessel and a solution of the carboxylation and hydrolysis catalysts is recycled and supplied to the carboxylation zone.

* * * * *